United States Patent
Yang et al.

(10) Patent No.: US 12,347,529 B1
(45) Date of Patent: Jul. 1, 2025

(54) METHOD OF ANALYZING THE COMPOSITION OF CIGARETTE LEAF GROUPS BASED ON FUSION MAPPING

(71) Applicant: CHINA TOBACCO YUNNAN INDUSTRIAL CO., LTD., Kunming (CN)

(72) Inventors: Ji Yang, Kunming (CN); Jianjun Xia, Kunming (CN); Baokun Zhu, Kunming (CN); Wei Zhang, Kunming (CN); Qianxu Yang, Kunming (CN); Qian Gao, Kunming (CN); Shiyun Tang, Kunming (CN); Wei Jiang, Kunming (CN); Juan Li, Kunming (CN); Chunbo Liu, Kunming (CN); Chunxia Yu, Kunming (CN); Kai Wu, Kunming (CN); Zhenjie Li, Kunming (CN)

(73) Assignee: CHINA TOBACCO YUNNAN INDUSTRIAL CO., LTD., Kunming (CN)

( * ) Notice: Subject to any disclaimer, the term of this patent is extended or adjusted under 35 U.S.C. 154(b) by 0 days.

(21) Appl. No.: 19/007,545

(22) Filed: Jan. 1, 2025

Related U.S. Application Data

(63) Continuation of application No. PCT/CN2024/082571, filed on Mar. 20, 2024.

(30) Foreign Application Priority Data

Mar. 19, 2024 (CN) .......................... 202410311499.1

(51) Int. Cl.
*G16C 20/20* (2019.01)
*G01N 33/02* (2006.01)

(52) U.S. Cl.
CPC .............. *G16C 20/20* (2019.02); *G01N 33/02* (2013.01)

(58) Field of Classification Search
CPC ................................ G16C 20/20; G01N 33/02
See application file for complete search history.

(56) References Cited

U.S. PATENT DOCUMENTS

| | | | |
|---|---|---|---|
| 2012/0250025 A1* | 10/2012 | Moshe | G01N 21/85 356/451 |
| 2014/0137877 A1* | 5/2014 | Deevi | B07C 5/342 356/303 |
| 2017/0265516 A1* | 9/2017 | Bovet | C12Y 304/22 |
| 2019/0343166 A1* | 11/2019 | Adams | C12N 15/8218 |
| 2023/0393106 A1* | 12/2023 | Xu | G01N 30/7206 |

FOREIGN PATENT DOCUMENTS

| | | |
|---|---|---|
| CN | 104568823 A | 4/2015 |
| CN | 110659691 A | 1/2020 |
| CN | 111543668 A | 8/2020 |
| CN | 116266475 A | 6/2023 |
| CN | 116665811 A | 8/2023 |

OTHER PUBLICATIONS

International Search Report, International Appl. No. PCT/CN2024/082571, Nov. 16, 2024, issued by the China National Intellectual Property Administration (ISA/CN), Beijing, China.
Written Opinion, International Appl. No. PCT/CN2024/082571, Nov. 16, 2024, issued by the China National Intellectual Property Administration (ISA/CN), Beijing, China.

* cited by examiner

*Primary Examiner* — Tung S Lau
(74) *Attorney, Agent, or Firm* — Central California IP Group, P.C.; Andrew D. Fortney

(57) ABSTRACT

The invention concerns a method for analyzing cigarette leaf components based on fusion mapping, including the following steps: (1) Preparation of a cigarette sample to be analyzed and single-grade tobacco leaf samples; (2) Construction of a fusion map for the cigarette sample to be analyzed and the single-grade tobacco leaf samples; (3) Analysis of the fusion map to obtain the composition and proportion of the tobacco leaves in the cigarette to be analyzed. The method can complete the analysis of the composition of finished cigarettes in a few minutes, and can obtain a clear formula composition and proportion values. It is objective, efficient, highly sensitive, and has good repeatability. It has unique advantages in the analysis of finished cigarette compositions in the tobacco industry.

15 Claims, No Drawings

METHOD OF ANALYZING THE COMPOSITION OF CIGARETTE LEAF GROUPS BASED ON FUSION MAPPING

CROSS-REFERENCE TO RELATED APPLICATIONS

This application is a continuation of International Pat. Appl. No. PCT/CN2024/082571, filed on Mar. 20, 2024, which claims the benefit of Chinese Pat. Appl. No. 202410311499.1, filed on Mar. 19, 2024, both of which are incorporated herein by reference as if fully set forth herein.

TECHNICAL FIELD

The invention belongs to the technical field of tobacco, in particular to a method for analyzing the composition of tobacco leaf groups based on fusion mapping.

BACKGROUND

The quality and style characteristics of cigarettes are mainly formed by product designers through the proportions of tobacco leaves of different origins, varieties and grades. It is usually necessary to rely on formula experience and sensory evaluation, and manually select 10-20 kinds of tobacco leaves from hundreds of stock grades of tobacco raw materials to design different formulas in different proportions. As a result, the composition of the coiled-tobacco leaf groups is extremely complicated, and it is difficult to analyze the composition of the unknown coiled-tobacco leaf groups manually. It is of great significance for the analysis of unknown tobacco and the design of leaf groups to analyze the composition of coiled tobacco leaves by means of instrument testing and using objective data and scientific technology.

In recent years, near infrared (NIR) technology has been widely used in tobacco quality analysis and evaluation, formulation design and maintenance because of its fast, efficient and abundant quality information. However, NIR analysis technology only considers the correlation between tobacco leaf quality and leaf composition under "static conditions," ignoring the quality characteristics under burning conditions during the consumption of cigarette products, and cannot truly represent the smoking quality of tobacco leaves, that is, the quality characteristics of smoke.

Thermogravimetric analysis (TG/DTA) can provide stable reaction conditions under programmed temperature conditions, and is the most ideal experimental tool for tobacco pyrolysis research. Derivative thermogravimetric methodology, also called the derivative thermogravimetric method, is derived from thermogravimetric analysis, and is a technique to record the first derivative of a TG curve with respect to temperature or time. The result of the experiment is a derivative thermogravimetric curve, that is, a DTG curve. The characteristics of DTG curves are: accurate reflection of the initial reaction temperature, maximum reaction rate temperature and reaction termination temperature of each weight loss stage; and the area of each peak on the DTG curve is proportional to the corresponding sample weight loss on the TG curve. When the TG curve is not obvious to some steps in the heating process, the DTG curve can be clearly distinguished. The main feature of thermogravimetric analysis is that it is highly quantitative and can accurately measure the mass change and the rate of change. It can be said that according to this feature, as long as the mass of a substance changes when it is heated, it can be studied by thermogravimetric analysis.

At present, the composition analysis of coiled tobacco leaves mostly adopts the combination of tobacco chemical composition analysis, flue gas chemical composition analysis, sensory evaluation and other means. Such analyses are highly intensive and subjective, and the conclusions drawn are vague and not referential.

In order to solve the above problems, the invention is proposed.

SUMMARY

In order to solve the existing problems of composition analysis of tobacco leaves, the invention concerns construction of a fusion map that can fully reflect tobacco quality by fusing a near-infrared spectrum and a thermal analysis map. Furthermore, a difference correlation model of the fusion map can be established to simulate and evaluate the coincidence between the analytic composition of the formula and the real leaf formula. In order to improve the generality of tobacco leaf group analysis and the work efficiency of analysts, the invention uses the fusion spectrum to analyze and characterize the quality information of shredded cigarette tobacco. The invention includes a fusion map, a difference correlation model and/or a formula analysis combination optimization algorithm to automatically search for the tobacco leaf ratio of the tobacco leaf group formula, using objective data to analyze the composition of the cigarette leaf group. The composition and proportion of the tobacco leaf group formula can be clearly obtained, which is of great significance to the analysis and design of tobacco leaf group formulas.

The invention provides a method for analyzing a tobacco leaf group composition based on fusion mapping. The specific steps are based on the ability of fusion maps to characterize tobacco qualities and to analyze the specific composition and formula ratio (i.e., the ratio of different single-grade tobacco leaves in the formula) of competing cigarettes (cigarettes to be analyzed) and other tobacco products.

The technical scheme of the invention is as follows:

A method for analyzing the composition and proportion of tobacco leaf groups in a cigarette sample includes the following steps: (1) preparing a tobacco (e.g., cigarette) sample to be analyzed and one or more single-grade tobacco leaf samples; (2) constructing a fusion map for the tobacco sample to be analyzed and the single-grade tobacco leaf sample(s); and (3) analyzing the fusion map to obtain the composition and proportion of tobacco leaves in the tobacco sample to be analyzed.

Preferably, in Step (1), there is a single tobacco (e.g., cigarette) sample to be analyzed, and at least 50 single-grade tobacco leaf samples analyzed. Each sample may be placed in a constant temperature and humidity environment of (22±1) ° C. and (60±2) % relative humidity for at least 48 hours for equilibrium. Generally, the tobacco sample is not less than 5 g, and the sample crushing mesh (e.g., screen) is not less than 100 mesh. Generally, no less than 50 typical single-grade tobacco samples are selected, and the single-grade tobacco samples should be of different grades, different origins and different parts (e.g., of the tobacco plant), and the smoking taste of typical single-grade tobacco samples is generally quite different.

Preferably, in Step (2), constructing the fusion map for the tobacco sample to be analyzed and the single-grade tobacco leaf samples includes the following sub-steps:

Sub-step (21), Collecting near-infrared spectra: placing a predetermined amount (e.g., 3 g) of the sample powder (e.g., of the tobacco sample to be analyzed, after crushing or screening and weighing) in a sample cup, scan the sample powder in the 4000-9000 cm$^{-1}$ band (e.g., of light, to obtain a near infrared [NIR] spectrum), and repeat the operation (e.g., 10 times for each of an identical number of samples of the tobacco to be analyzed) to obtain a spectral average;

Sub-step (22), Collecting a thermal analysis map: the samples are respectively heated in thermogravimetric (TG) crucibles by a procedure including: an initial temperature of 50° C., heating at a rate of 10° C./min to a final temperature of 900° C., and maintaining the temperature at 900° C. for 5 min, using a protection gas and reaction gas comprising nitrogen, at a flow rate of 20 mL/min. Taking temperature (° C.) as the X-axis and mass change (%) as the Y-axis, deriving the TG data (e.g., plotting a TG graph of the change in mass of the sample as a function of temperature), obtaining the first derivative (e.g., of the TG graph) with respect to temperature, obtaining derivative thermogravimetric (DTG) data (e.g., of differential weight loss), and making the thermal analysis map (e.g., by plotting mass change and/or DTG data as a function of temperature);

Sub-step (23), Constructing a fusion map: obtaining a matrix $A_{m \times n} = F_m \times F_n$ by multiplying an NIR spectral vector $F_m$ (including, e.g., NIR spectrum and/or spectral average data) of the sample (e.g., the tobacco sample[s] to be analyzed) and a thermal analysis spectrum vector $F_n$ (including, e.g., the thermal analysis map and/or data therein of the tobacco sample[s] to be analyzed), pooling a maximum by row vector $V_m = MAX_n(A_{m \times n}) = [v_1 \; v_2 \; \ldots \; v_i]$, and logarithmically normalizing $V_m$ to get a fusion of a sample mapping matrix $s_m =$ $$\left[ \frac{e^{v_1}}{\sum e^{v_1}} \; \frac{e^{v_2}}{\sum_{i=1}^{n} e^{v_2}} \; \cdots \; \frac{e^{v_i}}{\sum_{i=1}^{n} e^{v_i}} \right],$$

i=1, 2 ... m; and obtaining a fusion map matrix Y of the tobacco sample(s) to be analyzed and n single-grade tobacco leaf fusion map matrices $X=[X_1 \; X_2 \; \ldots \; X_n]$, where n is the number of single-grade tobacco samples (e.g., for which [i] NIR spectra or spectral averages and [ii] thermal analysis maps were collected).

Preferably, in Step (3), analyzing the fusion map to obtain the composition and proportion of the tobacco leaves in the tobacco sample to be analyzed includes the following sub-steps:

Sub-step (31), coding formula proportions: coding a real number for a proportion of each single grade tobacco leaf $R=[r_1 \; r_2 \; \ldots \; r_n]$ in one or more formulas, wherein n is the number of single-grade tobacco leaf samples described above;

Sub-step (32), randomly initializing the coding matrix R: initializing an r value $R_1, R_2, \ldots, R_{200}$ to a real value between 0 and 1, wherein a sum of the values in each coding matrix should be 1, establishing a search space (e.g., a library) according to a range of (e.g., including) more than 10 times the number of tobacco leaves composed of (e.g., in) the formula (e.g., a typical cigarette tobacco formula), and randomly initializing the coding matrix (that is, or for example, $R_1$, $R_2$, ... ). Since the number of tobacco leaves in a typical cigarette formula is generally 10-20, the search space according to the 10-fold (minimum) range includes at least 200 randomly initialized coding matrices (e.g., $R_1, R_2, \ldots R_{200}$);

Sub-step (33), calculating a tobacco sample fusion spectrum matrix Z after generating or calculating one or more combinations of single-grade tobacco leaves (e.g., according to the formula ratio[s]$R_1, R_2, \ldots$ in the coding matrix R);

Sub-step (34), calculating a difference value e between Z and Y by a difference correlation model of fusion maps;

Sub-step (35), Converting the difference value e to a probability value P(e);

Sub-step (36), according to the probability value, selecting a number of formula ratios or proportions (e.g., from among $R_1, R_2, \ldots$ ) to participate in a next iteration, randomly selecting two schemes (e.g., proportions of single grade tobacco leaves) for linear reorganization (or regression): $r^{(1)} = r_1 + a*(r_1 - r_2)$, and obtaining reorganized real number coding matrices $R_1^{(1)}, R_2^{(1)}, \ldots$, wherein a is a scale factor generated by random numbers that obey a [-d, 1+d] uniform distribution, and d is a value that limits the scope of the reorganization (or regression);

Sub-step (37), repeating sub-steps (32)-(34) (e.g., iterative searching), and iteratively calculating the difference value e (e.g., to generate $e^{(2)}, e^{(3)}, e^{(4)}, e^{(5)} \ldots$ on successive calculations) until e is less than a certain value; and Sub-step (38), ordering the probability value P(e) from largest to smallest, and taking a number of formula ratios or proportions (e.g., ranking a subset of the formula ratios $R_1, R_2, \ldots$ according to the corresponding probability value P(e) from largest to smallest), to obtain the tobacco composition and proportion of the tobacco to be analyzed (e.g., the formula ratio having the largest corresponding probability value P(e)).

Preferably, sub-step (32) should ensure that the sum of the values of each encoding matrix is 1, using an initialization formula as follows:

$$r_i = r_i / \sum_{i=1}^{n} r_i.$$

Preferably, in sub-step (33), to calculate the tobacco sample fusion map matrix Z after combining single-grade tobacco leaves according to the formula ratio R, the calculation formula is as follows: $Z_i = X' \times R_i$, where $R_i$ is the i-th random coding matrix, X (e.g., X') is the single-grade tobacco leaf fusion map matrix (e.g., the matrices corresponding to the single-grade tobacco leaves in the formula ratio R), and $Z_i$ is the formula fusion map matrix for (e.g., representing) formula ratio $R_i$.

Preferably, in sub-step (34), the formula for calculating the difference value e is as follows: $e = \sqrt{(Z-Y)\Sigma^{-1}(Z-Y)}$, where Y is the fusion map matrix of the tobacco sample to be analyzed, Z is the formula fusion map matrix for the tobacco leaves in proportion (e.g., according to the formula ratio $R_i$), and $\Sigma$ is a covariance matrix between Y and Z.

Preferably, in sub-step (35), the calculation formula to convert the difference value e to the probability value P(e) between 0 and 1 is:

$$P(e) = \frac{e_{max} - e}{e_{max} - e_{min}} / \text{sum}\left(\frac{e_{max} - e}{e_{max} - e_{min}}\right).$$

Preferably, in sub-step (36), d has a value of 0.2-0.3.

Preferably, in sub-step (37), e is iteratively calculated until it is <0.0001 (i.e., the certain value is 0.0001).

The invention has the following beneficial effects:

1. The method of the present invention may include a fusion mapping difference correlation model and a formula analysis combination and/or optimization algorithm, automatically searches for the tobacco leaf ratio in the tobacco leaf group formulas (e.g., the library of formula ratios in the coding matrix), can complete the composition analysis of any commercial cigarette within a few minutes, and can obtain a clear formula composition and proportion value, which is objective, efficient, versatile, and with good repeatability and high sensitivity. It has a unique advantage in the analysis of finished cigarettes in the tobacco industry.

2. The method of the present invention avoids wet chemical analysis of a large amount of tobacco, such as in conventional flue gas chemical composition analysis of tobacco leaf groups, and turns to dry chemical operation, which has the advantages of simplicity, minimal sample usage, accuracy (e.g., within 10 mg), non-toxicity and harmlessness, causes no harm to the operator, and no environmental pollution.

3. The method of the present invention not only provides a fusion spectrum of finished cigarettes to be analyzed (e.g., an analysis of the qualities thereof) and of single-grade tobacco leaves by near infrared and thermal analyses, but also greatly reduces the workload and the number of tests, provides concrete formula design objectives, rich data support and digital technical methodology for the development of cigarette products, and realizes an automatic search and objective evaluation of tobacco formula design schemes. It can avoid subjective factors and different representations that occur in traditional reliance on expert experience and sensory evaluation.

EXAMPLES

The present invention is further explained by embodiments below, but is not limited by the present embodiments. Experimental methods not specified in the embodiments are generally available commercially in accordance with conventional conditions, conditions described in the manual, or general equipment, materials, reagents, etc. used in accordance with conditions suggested by the manufacturer, unless otherwise specified. The raw materials in the following embodiments (and, e.g., in the applicable ratios) are commercially available.

Example: Method of analyzing the composition and proportion of tobacco leaf groups in a well-known domestic brand cigarette product (sample to be analyzed); the steps are as follows:

(1) A product sample of a well-known domestic brand of cigarettes (tobacco to be analyzed) and 50 single-grade tobacco samples of different origin, different parts and different grades of 5 grams each (e.g., of the tobacco to be analyzed and each of the single-grade tobacco leaves) were selected. The tobacco to be analyzed and the single-grade tobacco leaf samples were screened with a 100-mesh screen and treated for 48 hours in a constant temperature and humidity environment of (22±1)° C. and (60±2) % relative humidity.

(2) 3 g of each sample powder was weighed and placed in a sample cup, and scanned in the 4000-9000 $cm^{-1}$ band to create a near infrared (NIR) spectrum. The scanning was repeated 10 times for each sample to obtain a spectral average.

(3) Before the sample thermogravimetric analysis, the thermogravimetric analyzer was set and kept at 900° C. for 10 min to clear the impurities in the furnace body, and the empty crucible was used as a reference. A (5.00±0.05) mg sample was weighed and placed in a platinum thermogravimetric crucible, and the heating procedure was as follows: an initial temperature of 50° C., a heating rate of 10° C./min; a final temperature of 900° C., held at a constant temperature of 900° C. for 5 min. The protection gas and reaction gas were nitrogen, and the flow rate was 20 mL/min. Taking temperature (° C.) as one axis (e.g., the X-axis) and mass change (%) as an orthogonal axis (e.g., the Y-axis), the TG data were derived (e.g., a curve plotting the mass change as a function of temperature was created), then the first derivative of the TG (e.g., mass change) data as a function of temperature was obtained to obtain DTG data (e.g., of differential weight loss, optionally as a curve plotting the first derivative of the mass change as a function of temperature), and the thermal analysis map was formed (e.g., from the TG and/or DTG data and/or curve[s]).

The tobacco sample fusion map matrix Y and the single grade tobacco fusion matrix atlas/library $X=[X_1\ X_2\ \ldots\ X_{50}]$ were calculated, where the number of variables (e.g., mass change data points) in the fusion map matrix is m:

TABLE 1

| Tobacco sample (to be analyzed) fusion map matrix Y | | | | | |
|---|---|---|---|---|---|
| $y_1$ | $y_2$ | $y_3$ | $y_4$ | ... | $y_m$ |
| Tobacco to be analyzed 2.65E–05 | 3.85E–05 | 3.42E–05 | 2.02E–05 | ... | 5.48E–05 |

TABLE 2

| Single grade tobacco fusion map matrices X | | | | | |
|---|---|---|---|---|---|
| $x_1$ | $x_2$ | $x_3$ | $x_4$ | ... | $x_m$ |
| Tobacco leaf 1 ($X_1$) 3.86E–05 | 3.86E–05 | 4.51E–05 | 1.07E–05 | ... | 3.94E–05 |
| Tobacco leaf 2 ($X_2$) 2.53E–05 | 2.53E–05 | 5.27E–05 | 1.73E–05 | ... | 2.23E–05 |
| ... | ... | ... | ... | ... | ... |
| Tobacco leaf 50 ($X_{50}$) 2.77E–05 | 2.77E–05 | 4.72E–05 | 1.96E–05 | ... | 1.78E–05 |

(4) The formula ratio real number coding matrix $R=[r_1\ r_2\ \ldots\ r_{50}]$ is set, where $r_1, r_2, \ldots, r_{50}$ represents the proportion or ratio of 50 single-grade tobacco leaves in the formulation, as shown in Table 3:

TABLE 3

Formula proportional real number coding matrix R

| Single grade tobacco | Formula ratio $r_i$ |
|---|---|
| Tobacco leaf 1 | $r_1$ |
| Tobacco leaf 2 | $r_2$ |
| ... | ... |
| Tobacco leaf 50 | $r_{50}$ |

The proportion or ratio of single-grade tobacco leaves $r_i$ in the above table is initialized randomly to a real value between 0 and 1, and $r_i$ is subsequently normalized to ensure that the sum of proportion values of each tobacco leaf in the formula is 1. The formula is as follows:

$$r_i = r_i \Big/ \sum_{i=1}^{n} r_i.$$

where n is 50.

TABLE 4

Random initialization results of formula proportional real number coding matrix R

| Single grade tobacco | Formula ratio $r_i$ |
|---|---|
| Tobacco leaf 1 | 0.05 |
| Tobacco leaf 2 | 0.02 |
| ... | ... |
| Tobacco leaf 50 | 0.26 |
| Total | 1.00 |

According to the above method, 200 real number coding matrices $R_1, R_2, \ldots R_{200}$ are initialized at the same time to establish a formula library (e.g., a search space) for analytic searching, as shown in the following table:

TABLE 5

Real number coding initialization of formula proportions/ratios

| Coding | $R_1$ | $R_2$ | $R_3$ | $R_4$ | ... | $R_{200}$ |
|---|---|---|---|---|---|---|
| $r_1$ | 0.05 | 0.14 | 0.02 | 0.00 | ... | 0.12 |
| $r_2$ | 0.02 | 0.02 | 0.01 | 0.16 | ... | 0.14 |
| $r_3$ | 0.04 | 0.03 | 0.02 | 0.22 | ... | 0.02 |
| $r_4$ | 0.03 | 0.05 | 0.08 | 0.06 | ... | 0.03 |
| ... | ... | ... | ... | ... | ... | ... |
| $r_{50}$ | 0.26 | 0.04 | 0.08 | 0.08 | ... | 0.09 |
| Total | 1.00 | 1.00 | 1.00 | 1.00 | 1.00 | 1.00 |

The tobacco fusion map matrix Z (e.g., an atlas or library of tobacco formula fusion maps with randomly initiated values) is calculated by combining single-grade tobacco fusion maps in the matrix X according to the proportions/ratios in the formulas in the real number coding matrix R (e.g., $Z_i = X' \times R_i$):

TABLE 6

Tobacco fusion map matrix Z after combination from single-grade tobacco fusion maps

| | $z_1$ | $z_2$ | $z_3$ | $z_4$ | ... | $z_m$ |
|---|---|---|---|---|---|---|
| $Z_1$ | 4.58E–05 | 5.14E–05 | 1.17E–05 | 2.56E–05 | ... | 4.71E–05 |
| $Z_2$ | 1.27E–05 | 8.43E–06 | –2.64E–05 | 8.65E–06 | ... | 1.12E–05 |
| ... | ... | ... | ... | ... | ... | ... |
| $Z_{200}$ | 5.25E–05 | 4.78E–05 | 2.15E–05 | 2.05E–05 | ... | 2.86E–05 |

A difference correlation model of the fusion map, $e = \sqrt{(Z-Y)\Sigma^{-1}(Z-Y)}$, is used to calculate the difference value e between Z and Y, so as to evaluate the conformity of the composition analysis of the tobacco leaf groups (e.g., to determine a difference between the tobacco sample fusion map matrix Y and each of the tobacco fusion maps in the matrix Z, as shown in Table 7 below:

TABLE 7

Analytical coincidence (difference between Z and Y) of tobacco composition fusion maps

| Candidate | $R_1$ | $R_2$ | $R_3$ | $R_4$ | ... | $R_{200}$ |
|---|---|---|---|---|---|---|
| Difference e | 4.4703 | 3.5132 | 7.18698 | 2.0721 | ... | 1.9468 |

The difference values e are converted to a probability value P(e) using the $$\text{formula } P(e) = \frac{e_{max} - e}{e_{max} - e_{min}} \Big/ \text{sum}\left(\frac{e_{max} - e}{e_{max} - e_{min}}\right),$$

as shown in Table 8 below:

TABLE 8

Convert the difference value e to a probability value

| Candidate | $R_1$ | $R_2$ | $R_3$ | $R_4$ | ... | $R_{200}$ | Total |
|---|---|---|---|---|---|---|---|
| Probability value P(e) | 0.51% | 0.76% | 0.59% | 1.21% | ... | 1.12% | 100% |

The first 100 candidates for the formula ratio were selected randomly and/or according to the probability values (e.g., the tobacco fusion maps in the matrix Z having the highest probability value), and the formula ratios of the candidates were reorganized linearly in pairs (or analyzed pairwise by linear regression) according to the equation $r^{(1)} = r_1 + a*(r_1 - r_2)$, where a is a scale factor, generated by random numbers with a uniform distribution following [–d, 1+d], where d is 0.25, a value that limits the reorganization (or regression) range to within a manageable range or distribution (e.g., so that it is not too large).

The reorganized real number coding matrix $R_1^{(1)}, R_2^{(1)}, \ldots R_{200}^{(1)}$ is obtained as shown in Table 9 below:

TABLE 9

Real number codes of formula ratios after reorganization

| Code | $R_1^{(1)}$ | $R_2^{(1)}$ | $R_3^{(1)}$ | $R_4^{(1)}$ | ... | $R_{200}^{(1)}$ |
|---|---|---|---|---|---|---|
| $r_1$ | 0.00 | 0.04 | 0.20 | 0.06 | ... | 0.15 |
| $r_2$ | 0.15 | 0.12 | 0.05 | 0.15 | ... | 0.06 |
| $r_3$ | 0.05 | 0.15 | 0.06 | 0.12 | ... | 0.08 |

TABLE 9-continued

Real number codes of formula ratios after reorganization

| Code | $R_1^{(1)}$ | $R_2^{(1)}$ | $R_3^{(1)}$ | $R_4^{(1)}$ | ... | $R_{200}^{(1)}$ |
|---|---|---|---|---|---|---|
| $r_4$ | 0.09 | 0.25 | 0.12 | 0.05 | ... | 0.02 |
| ... | ... | ... | ... | ... | ... | ... |
| $r_{50}$ | 0.03 | 0.02 | 0.20 | 0.04 | ... | 0.08 |
| Total | 1.00 | 1.00 | 1.00 | 1.00 | 1.00 | 1.00 |

According to the real number coding of the reorganized formula proportions or ratios, a reorganized tobacco sample fusion map matrix Z(1) was calculated. The fusion map difference association model was invoked to calculate the difference value $e^{(1)}$ between Z (e.g., the tobacco sample fusion map matrix Z or the reorganized tobacco sample fusion map matrix Z(1)) and Y, and the difference value e was iteratively calculated (e.g., to generate $e^{(2)}$, $e^{(3)}$, $e^{(4)}$, $e^{(5)}$, ...) until e<0.0001 (in this example, until e=0.000095).

According to the probability value P(e) from large to small, the top 5 formula proportional candidates are output, as shown in Table 10 below:

TABLE 10

Formula analysis results and P(e) values (the top 5 candidates with the highest probability values are selected)

| Code | $R_{172}^{(1)}$ | $R_{26}^{(1)}$ | $R_{23}^{(1)}$ | $R_{31}^{(1)}$ | $R_{156}^{(1)}$ |
|---|---|---|---|---|---|
| $r_1$ | 0.00 | 0.00 | 0.00 | 0.00 | 0.00 |
| $r_2$ | 0.00 | 0.02 | 0.00 | 0.08 | 0.05 |
| $r_3$ | 0,20 | 0.25 | 0.20 | 0.12 | 0.06 |
| $r_4$ | 0.15 | 0.15 | 0,05 | 0.10 | 0.25 |
| ... | ... | ... | ... | ... | ... |
| $r_{50}$ | 0.05 | 0.08 | 0.15 | 0.12 | 0.08 |
| P(e) | 72.05% | 13.25% | 4.45% | 2.20% | 1.15% |

According to the first five formula ratio candidates in the above table, tobacco leaves with a formula ratio of 0 are filtered out to obtain the complete composition and ratio of the tobacco leaf formula, as shown in Tables 11-15 below:

TABLE 11

Leaf formula corresponding to $R_{172}$

| Single grade tobacco | Formula ratio |
|---|---|
| Tobacco Leaf 3 | 0.20 |
| Tobacco Leaf 4 | 0.15 |
| Tobacco Leaf 11 | 0.05 |
| Tobacco Leaf 18 | 0.05 |
| Tobacco Leaf 30 | 0.06 |
| Tobacco Leaf 31 | 0.10 |
| Tobacco Leaf 35 | 0.10 |
| Tobacco Leaf 37 | 0.05 |
| Tobacco Leaf 40 | 0.05 |
| Tobacco Leaf 42 | 0.05 |
| Tobacco Leaf 45 | 0.05 |
| Tobacco Leaf 47 | 0.02 |
| Tobacco Leaf 49 | 0.02 |
| Tobacco Leaf 50 | 0.05 |

TABLE 12

Leaf formulations corresponding to $R_{26}$

| Single grade tobacco | Formula ratio |
|---|---|
| Tobacco Leaf 2 | 0.02 |
| Tobacco Leaf 3 | 0.25 |
| Tobacco Leaf 4 | 0.15 |
| Tobacco Leaf 18 | 0.05 |
| Tobacco Leaf 30 | 0.02 |
| Tobacco Leaf 31 | 0.05 |
| Tobacco Leaf 35 | 0.02 |
| Tobacco Leaf 37 | 0.02 |
| Tobacco Leaf 40 | 0.05 |
| Tobacco Leaf 42 | 0.06 |
| Tobacco Leaf 45 | 0.10 |
| Tobacco Leaf 47 | 0.08 |
| Tobacco Leaf 49 | 0.05 |
| Tobacco Leaf 50 | 0.08 |

TABLE 13

Leaf formulations corresponding to $R_{23}$

| Single grade tobacco | Formula ratio |
|---|---|
| Tobacco Leaf 3 | 0.2 |
| Tobacco Leaf 4 | 0.05 |
| Tobacco Leaf 18 | 0.08 |
| Tobacco Leaf 30 | 0.15 |
| Tobacco Leaf 31 | 0.05 |
| Tobacco Leaf 35 | 0.05 |
| Tobacco Leaf 37 | 0.02 |
| Tobacco Leaf 40 | 0.04 |
| Tobacco Leaf 42 | 0.07 |
| Tobacco Leaf 45 | 0.06 |
| Tobacco Leaf 47 | 0.10 |
| Tobacco Leaf 49 | 0.05 |
| Tobacco Leaf 50 | 0.08 |

TABLE 14

Leaf formulations corresponding to $R_{31}$

| Single grade tobacco | Formula ratio |
|---|---|
| Tobacco Leaf 2 | 0.08 |
| Tobacco Leaf 3 | 0.12 |
| Tobacco Leaf 4 | 0.10 |
| Tobacco Leaf 8 | 0.04 |
| Tobacco Leaf 13 | 0.10 |
| Tobacco Leaf 18 | 0.02 |
| Tobacco Leaf 19 | 0.18 |
| Tobacco Leaf 25 | 0.01 |
| Tobacco Leaf 28 | 0.08 |
| Tobacco Leaf 29 | 0.08 |
| Tobacco Leaf 40 | 0.03 |
| Tobacco Leaf 42 | 0.04 |
| Tobacco Leaf 50 | 0.12 |

TABLE 15

Leaf formulations corresponding to $R_{156}$

| Single grade tobacco | Formula ratio |
|---|---|
| Tobacco Leaf 2 | 0.05 |
| Tobacco Leaf 3 | 0.06 |
| Tobacco Leaf 4 | 0.25 |
| Tobacco Leaf 5 | 0.05 |
| Tobacco Leaf 12 | 0.05 |
| Tobacco Leaf 14 | 0.05 |
| Tobacco Leaf 15 | 0.02 |
| Tobacco Leaf 19 | 0.02 |
| Tobacco Leaf 20 | 0.06 |
| Tobacco Leaf 21 | 0.04 |

TABLE 15-continued

Leaf formulations corresponding to $R_{156}$

| Single grade tobacco | Formula ratio |
| --- | --- |
| Tobacco Leaf 22 | 0.04 |
| Tobacco Leaf 25 | 0.08 |
| Tobacco Leaf 28 | 0.03 |
| Tobacco Leaf 29 | 0.05 |
| Tobacco Leaf 31 | 0.02 |
| Tobacco Leaf 40 | 0.02 |
| Tobacco Leaf 42 | 0.04 |
| Tobacco Leaf 50 | 0.07 |

Verification experiment: According to the five formulations shown in Tables 11-15, the corresponding single-grade tobacco leaf samples were mixed into cigarettes, and 9 sensory evaluation experts evaluated and scored the sensory quality differences between the mixed tobacco sample and the cigarette sample to be analyzed according to the gradient or scores shown in Table 16 below. The average value was taken as the actual smoking evaluation value of the quality difference(s), and the quality difference(s) were rounded and converted to the corresponding qualitative evaluation shown in Table 16.

TABLE 16

Sensory quality difference score gradient setting

| Quality deviation | None | slight | lesser | Intermediate | big | Large |
| --- | --- | --- | --- | --- | --- | --- |
| Score | 0 | 1 | 2 | 3 | 4 | 5 |

The smoking evaluation results are shown in Table 17 below:

TABLE 17

Verification results of sensory evaluation

| Candidate formulation | P(e) | Average | Quality difference |
| --- | --- | --- | --- |
| $R_{172}$ | 72.05% | 0.00 | None |
| $R_{26}$ | 13.25% | 0.33 | Slight |
| $R_{23}$ | 4.45% | 0.44 | Slight |
| $R_{31}$ | 2.20% | 0.89 | Slight |
| $R_{156}$ | 1.15% | 1.44 | Slight |

As can be seen from Table 17, the consistency between formula ratio candidate $R_{172}$ and the cigarette to be analyzed was 72.05%, and there was no difference in sensory evaluation results. The coincidence between candidates $R_{26}$, $R_{23}$, $R_{31}$, $R_{156}$ and the cigarette to be analyzed were 13.25%, 4.45%, 2.20% and 1.15%, respectively, and the results of sensory evaluation were slightly different.

The above embodiments disclose only several embodiments of the invention, and their descriptions are more specific and detailed, but they cannot be construed as limitations on the scope of the invention. It should be noted that for ordinary technicians in the field, without deviating from the concepts of the invention, a number of derivations and improvements can be made that are within the scope of protection of the invention. Therefore, the scope of protection of the invention patent shall be subject to the attached claims.

What is claimed is:

1. A method for analyzing a composition and proportion of tobacco leaves in a cigarette sample based on fusion mapping, comprising: preparing a cigarette sample to be analyzed and a plurality of single-grade tobacco leaf samples; constructing a fusion map for the cigarette sample to be analyzed and the plurality of single-grade tobacco leaf samples; and analyzing the fusion map to obtain the composition and proportion of the tobacco leaves among the single-grade tobacco leaf samples in the cigarette sample to be analyzed, wherein analyzing the fusion map comprises:

coding a real number for a formula proportion of each single grade tobacco leaf $R=[r_1\ r_2 \ldots r_n]$, where n is the number of single-grade tobacco leaf samples;

randomly initializing a coding matrix by initializing a value of r to a real value between 0 and 1, where a sum of the values in each coding matrix is 1;

establishing a search space according to a range of more than 10 times a number of tobacco leaves composed of a formula of the formula proportion, and randomly initializing a coding matrix $R_1, R_2, \ldots$;

calculating a cigarette fusion spectrum matrix Z after combining single-grade tobacco leaves in accordance with the formulation ratio R;

calculating a difference value e between Z and a fusion map matrix Y of the cigarette sample to be analyzed by a difference correlation model of fusion maps;

converting the difference value e to a probability value P(e);

according to the probability value, selecting a number of formula proportions to participate in a next iteration, randomly selecting two schemes for linear reorganization: $r^{(1)}=r_1+a*(r_1-r_2)$, and obtaining reorganized real number coding matrices $R_1^{(1)}, R_2^{(1)}, \ldots$, wherein a is a scale factor generated by random numbers that obey a [−d, 1+d] uniform distribution, and d is a value that limits a scope of reorganization;

repeating randomly initializing the coding matrix, calculating the cigarette fusion spectrum matrix Z, and calculating the difference value e between Z and Y for iterative searching, and iteratively calculating $e^{(2)}$, $e^{(3)}$, $e^{(4)}$, $e^{(5)}$ . . . until e is less than a certain value; and ordering the probability value P(e) from largest to smallest, taking a number of the formula proportions, and obtaining the tobacco composition and proportion of the tobacco leaves among the single-grade tobacco leaf samples in the cigarette to be analyzed.

2. The method of claim 1, wherein the value of r is initialized with a formula $$r_i = r_i / \sum_{i=1}^{n} r_i.$$

3. The method of claim 1, wherein calculating the cigarette fusion map matrix Z after combining single-grade tobacco leaves according to the formulation ratio R comprises calculating the cigarette fusion spectrum matrix Z by a formula: $Z_i = X' \times R_i$, wherein $R_i$ is the i-th coding matrix, X is a tobacco fusion map matrix, and $Z_i$ is a formula fusion map matrix composed of formula proportion $R_i$.

4. The method of claim 1, wherein the difference value e is calculated by a formula: $e=\sqrt{(Z-Y)\Sigma^{-1}(Z-Y)}$, wherein Y is the fusion map matrix of the cigarette to be analyzed, Z is the formula fusion map matrix composed of tobacco leaves in proportion, and Σ is a covariance matrix between Y and Z.

5. The method of claim 1, wherein a calculation formula to convert the difference value e value to the probability value P(e) between 0 and 1 is:

$$P(e) = \frac{e_{max} - e}{e_{max} - e_{min}} / \text{sum}\left(\frac{e_{max} - e}{e_{max} - e_{min}}\right).$$

6. The method of claim 1, wherein d has a value of 0.2-0.3.

7. The method of claim 1, wherein e is iteratively calculated until it is <0.0001.

8. The method of claim 1, wherein a single cigarette sample to be analyzed and at least 50 single-grade tobacco leaf samples are prepared.

9. The method of claim 8, wherein preparing the single cigarette sample to be analyzed and the at least 50 single-grade tobacco leaf samples comprises placing each sample in a constant temperature and humidity environment of (22±1) °C. and (60±2) % relative humidity for at least 48 hours.

10. The method of claim 8, wherein randomly initializing the coding matrix includes:
weighing a powder of each of the tobacco sample to be analyzed and the at least 50 single-grade tobacco leaf samples, placing them separately in respective sample cups, and scanning a spectrum of each sample in a 4000-9000 cm$^{-1}$ band, repeating the scanning to obtain a spectral average for each sample;
collecting a thermal analysis map by respectively placing each of the samples in thermogravimetric (TG) crucibles and heating to derive TG data, obtaining a first derivative of temperature, then obtaining derivative thermogravimetric (DTG) data of differential weight loss, and forming the thermal analysis map; and
obtaining a matrix $A_{m \times n}$ by multiplying a near infrared (NIR) spectral vector including data of the corresponding spectral average and a thermal analysis spectrum vector including data of the corresponding thermal analysis map, pooling a maximum by row vector of the matrix $A_{m \times n}$, and logarithmically normalizing the maximum by row vector to obtain a fusion map matrix Y of the cigarette sample to be analyzed and n single-grade tobacco leaf fusion map matrices, where n is the number of the single-grade tobacco samples and is at least 50.

11. The method of claim 10, wherein 3 g of the powder of each of the tobacco sample to be analyzed and the at least 50 single-grade tobacco leaf samples is weighed.

12. The method of claim 10, wherein, the scanning is repeated 10 times for each sample.

13. The method of claim 10, wherein the matrix $A_{m \times n}$ equals $F_m \times F_n$, wherein $F_m$ is the near infrared (NIR) spectral vector and $F_n$ is the thermal analysis spectrum vector, the maximum by row vector $V_m$ equals $\text{MAX}_n(A_{m \times n}) = [v_1\ v_2\ \ldots\ v_i]$, and logarithmically normalizing $V_m$ provides a fusion of a sample mapping matrix $$s_m = \left[\frac{e^{v_1}}{\sum_{i=1}^{n} e^{v_1}} \frac{e^{v_2}}{\sum_{i=1}^{n} e^{v_2}} \cdots \frac{e^{v_i}}{\sum_{i=1}^{n} e^{v_i}}\right],$$

=1, 2, . . . , m to obtain the fusion map matrix Y of the cigarette sample to be analyzed and the n single-grade tobacco leaf fusion map matrices.

14. The method of claim 12, wherein the samples in the TG crucibles are heated according to a procedure including an initial temperature of 50° C., a heating rate of 10° C./min, a final temperature of 900° C., and a constant temperature at 900° C. for 5 min using nitrogen at a flow rate of 20 mL/min.

15. The method of claim 14, wherein the TG data is derived by taking temperature (° C.) as an X-axis and mass change (%) as a Y-axis.

\* \* \* \* \*